United States Patent
Giglia

(10) Patent No.: US 10,955,328 B2
(45) Date of Patent: Mar. 23, 2021

(54) MIXED GAS INTEGRITY TESTING OF POROUS MATERIALS WITHOUT PERMEATE SIDE ACCESS

(71) Applicant: EMD Millipore Corporation, Burlington, MA (US)

(72) Inventor: Salvatore Giglia, Bedford, MA (US)

(73) Assignee: EMD Millipore Corporation, Burlington, MA (US)

(*) Notice: Subject to any disclaimer, the term of this patent is extended or adjusted under 35 U.S.C. 154(b) by 47 days.

(21) Appl. No.: 16/349,855

(22) PCT Filed: Nov. 20, 2017

(86) PCT No.: PCT/US2017/062518
§ 371 (c)(1),
(2) Date: May 14, 2019

(87) PCT Pub. No.: WO2018/156223
PCT Pub. Date: Aug. 30, 2018

(65) Prior Publication Data
US 2019/0277744 A1     Sep. 12, 2019

Related U.S. Application Data

(60) Provisional application No. 62/461,920, filed on Feb. 22, 2017.

(51) Int. Cl.
*G01N 15/08*     (2006.01)
*G01N 33/00*     (2006.01)
(Continued)

(52) U.S. Cl.
CPC ......... *G01N 15/082* (2013.01); *B01D 65/102* (2013.01); *G01N 33/0011* (2013.01);
(Continued)

(58) Field of Classification Search
CPC ............... G01N 15/082; G01N 33/011; G01N 2015/0662; G01N 2015/084;
(Continued)

(56) References Cited

U.S. PATENT DOCUMENTS 7,594,425 B2     9/2009  Lewnard et al.
9,108,138 B2     8/2015  Hao et al.
(Continued)

FOREIGN PATENT DOCUMENTS

JP     H04-142445 A     5/1992
JP     2002-45661 A     2/2002
(Continued)

OTHER PUBLICATIONS

International Search Report and Written Opinion received for PCT Application No. PCT/US2017/062518, dated Jan. 18, 2018, 5 pages.
(Continued)

*Primary Examiner* — John Fitzgerald
*Assistant Examiner* — Rodney T Frank
(74) *Attorney, Agent, or Firm* — EMD Millipore Corporation

(57) ABSTRACT

A method of integrity testing porous materials that is non-destructive to the material being tested. The inlet gas stream includes at least two gases, wherein one of the gases has a different permeability in liquid than the other, such as oxygen and nitrogen in water. The relative permeability of the gases is measured in the retentate stream, thereby avoiding accessing the permeate stream and potentially introducing contaminants to the material being tested. The integrity test is capable of detecting the presence of over-sized pores or defects that can compromise the retention capability of the porous material.

6 Claims, 1 Drawing Sheet

(51) Int. Cl.
  *B01D 65/10* (2006.01)
  *G01N 15/06* (2006.01)
(52) U.S. Cl.
  CPC ...... *B01D 2311/24* (2013.01); *B01D 2325/02* (2013.01); *G01N 2015/0662* (2013.01); *G01N 2015/084* (2013.01); *G01N 2033/0019* (2013.01)
(58) Field of Classification Search
  CPC ............ G01N 2033/0019; B01D 5/102; B01D 2311/24; B01D 2335/02
  USPC .......................................................... 73/38
  See application file for complete search history.

(56) References Cited

U.S. PATENT DOCUMENTS

| | | |
|---|---|---|
| 2007/0089489 A1 | 4/2007 | Lewnard et al. |
| 2013/0019658 A1 | 1/2013 | Hao et al. |

FOREIGN PATENT DOCUMENTS

| | | |
|---|---|---|
| JP | 2013-226542 A | 11/2013 |
| JP | 2014-504732 A | 2/2014 |
| WO | 2017/087057 A1 | 5/2017 |
| WO | 2018/156223 A1 | 8/2018 |

OTHER PUBLICATIONS

Giglia et al., "High Sensitivity Binary Gas Integrity Test for Membrane Filters", Journal of Membrane Science, vol. 323, Oct. 1, 2008, pp. 60-66.

MIXED GAS INTEGRITY TESTING OF POROUS MATERIALS WITHOUT PERMEATE SIDE ACCESS

RELATED APPLICATIONS

The present application is a US National Stage application of International Application No. PCT/US2017/062518, filed Nov. 20, 2017, which claims the benefit of priority of U.S. Provisional Application Ser. No. 62/461,920 filed Feb. 22, 2017, the disclosure of each of which is incorporated herein by reference in its entirety.

FIELD OF THE DISCLOSURE

The embodiments disclosed herein generally relate to a method for integrity testing porous media.

BACKGROUND

High purity filtration of aqueous media, such as in the fields of biotechnology, chemistry, electronics, pharmaceuticals, and the food and beverage industries requires the use of sophisticated filter modules that are not only capable of a high degree of separation, but that will tend to prevent contamination of the environment, of the medium to be filtered, and of the resulting filtrate. This is designed to prevent unwanted, often dangerous organisms, such as bacteria or viruses, as well as environmental contaminants, such as dust, dirt, and the like, from entering into the process stream and end product. To ensure that the sterility and/or retention capability of the porous material responsible for the filtration is not compromised, integrity testing is a fundamental requirement of critical process filtration applications.

For example, FDA guidelines recommend integrity testing of filter modules prior to use and after filtration. Typically this testing is initially performed after steam sterilization to ensure that the filter is not damaged; accordingly, care must be taken to ensure that sterility of the filter, and thus the filtrate, is not compromised. Post-processing, the filter integrity test is performed again in situ to detect whether the filter was compromised during use. This information can be used to alert operators to a potential problem immediately after processing, and to quickly take corrective action. Further, FDA guidelines require that integrity testing documentation be included with batch product records.

There are a variety of methods of integrity testing to detect the presence of oversized pores or defects that can compromise the retention capability of porous materials, including the particle challenge test, the liquid-liquid porometry test, the diffusion test, the bubble point test, the gas-liquid diffusion test and diffusion tests measuring tracer components. Some of these tests, such as the particle challenge test, are destructive, and therefore cannot be used as a pre-use test. Gas-liquid diffusion tests often lack sensitivity for detecting small defects, due to the inherent background noise in these tests. Liquid-liquid porometry and bubble point tests are useful for ensuring that a membrane with the proper nominal pore size is installed, but lack sensitivity for identifying small numbers of small defects.

Also known in the art is the binary gas test, where two gases of differing permeabilities are driven through the liquid layer of a wetted filter. This test allows for improved defect detection sensitivity compared to the single gas diffusion test and other integrity tests. A sweep flow of the binary gas pair on the upstream side of the membrane to maintain a constant composition on the upstream (inlet) side of the filter is used. A pressure differential between the upstream and downstream side of the filter is established by elevating the pressure of the inlet gas. The concentration of the gases on the downstream (permeate) side of the filter (enriched in the faster permeating gas) is then measured, and this measured value is compared to a known expected value from an integral filter. A deviation from the expected value is indicative of a defect in the filter being tested.

The binary gas test has been described in the art. As noted above, the tests described in the art rely on measurement of the gas concentration on the downstream side of the filter. However, it is often desirable to limit external access to the downstream side of the filter to eliminate the possibility of introducing contamination, since the filter itself would capture any potential contaminants from entering the filtrate side. Automated integrity testers that are based on the diffusive flow or bubble point methods typically access only the upstream side of the filter, using the pressure decay method, to assess filter integrity.

Another advantage of measuring the properties of upstream side gas is that, unlike the downstream side, the gas is not saturated in the fluid used to wet the filter. Vapor in a gas saturated with the wetting fluid (often water) can interfere with flow or composition measurements, particularly if any condensation occurs. The upstream gas in the binary gas test is often at elevated pressure, but for measurement purposes, the sampled gas can be throttled down to a lower pressure, thereby eliminating the risk of condensation of the sampled gas.

Another drawback of the prior art is that the sample size or the sampling rate of the permeated gas is limited by the diffusive flow rate of the gas across the filter. This limitation may be overcome to an extent by adding equipment and complexity to the process.

In accordance with conventional practice, assessing the integrity of a porous material includes:
  a) wetting the porous material with a liquid;
  b) contacting a first surface of the porous material with a gas mixture comprising two or more gases, where at least one of the gases in the mixture has a different permeability in the liquid compared to the other gases in the mixture;
  c) applying a pressure to the first surface of the porous material such that the gas mixture permeates through the porous material;
  d) measuring the steady state concentration of at least one of the gases in the gas mixture permeate in an area proximal to a second surface of the porous material; and
  e) comparing the steady state concentration with a predetermined concentration,
wherein a difference in the steady state concentration and the predetermined concentration is indicative of a non-integral porous material. Another conventional method recirculates the permeate side gas to accelerate sampling time, and also relies on assessing the concentration of the gas mixture on the permeate side.

Assessing the downstream (permeate) side of the porous material for measurement of gas concentration can be problematic for a number of reasons. One issue is that it is often desirable to avoid any possibility of introducing contaminants to the filtrate (product) side of the filter. In a sterilizing grade filter, for example, it is imperative that sterility is maintained on the filtrate side immediately prior to the start of the filtration. If the filter is integrity tested before filtration, access to the filtrate side is thus undesirable. For this reason, an upstream side pressure decay method is often used to determine the diffusive flow rate across the filter in a gas/liquid diffusion integrity test.

The permeate gas in a binary gas integrity test is usually saturated with the fluid (typically water) that is used to wet the filter. Gas saturated with the wetting fluid vapor is vulnerable to condensation, and the vapor (condensed or not) can interfere with measurements of gas concentration and flow rate. To avoid vapor and condensation effects on flow and concentration measurements, the vapor concentration can be reduced, such as with the use of a desiccant, for example. The addition of a desiccant, however, has its own drawbacks including added cost, complexity, and added volume.

Another issue with concentration measurement from the permeate side is that the sampling rate is limited by the diffusive flow rate across the membrane. Instrumentation used to measure gas concentration (such as an oxygen analyzer, for example) requires a minimum flow rate or sample size to provide accurate results. In cases where the diffusive flow rate is relatively low, the sample size or flow rate may not be sufficient for concentration measurement.

In light of the above, a need exists for an integrity test method for filters that provides the advantages of the binary gas integrity test for porous materials, but requires that only the upstream side of the filter be accessed for assessing the filter integrity. Sampling from the upstream side has the added advantage that the sampling rate can be easily controlled.

SUMMARY

Problems of the prior art are addressed by the embodiments disclosed herein, which include a method of integrity testing porous materials that eliminates the need to sample from the permeate side of the porous material being tested. In certain embodiments, only the upstream side of the filter is accessed for all gas composition measurements. In some embodiments, the composition of the retentate (non-permeate) gas is used to assess the integrity of the filter. The integrity test is capable of detecting the presence of oversized pores or defects that can compromise the retention capability of the porous material. The sample flow rate can be set to a desired value independent of the permeate flow rate.

In certain embodiments, the porous material is a sterilizing grade filter, i.e., filters capable of retaining B. diminuta at a challenge level of $10^7$ cfu/cm$^2$ per ASTM F838-15a.

In certain embodiments, the integrity test is rapid, sensitive, non-destructive, inexpensive, not deleterious to the environment, and easy to carry out. It provides a sensitive and reliable assessment of the integrity of the porous material or element.

The gases that are measured are not near their dew points, minimizing the probability of condensation and interference with flow and concentration measurements. Sample flow can be set to a desired value that is independent of the permeate flow rate.

In some embodiments, the method of integrity testing a porous material includes providing a porous material to be tested, the porous material having an upstream side and a filtrate side; providing a gas stream comprising at least first and second gases having different permeabilities in a liquid used to wet the porous material; introducing that gas stream to the upstream side of the porous material; causing the first and second gases to flow through the porous material; measuring the concentration of at least one of the first and second gases in a retentate stream exiting the upstream side of the porous material; and comparing the measured concentration to a predetermined concentration; wherein a difference between the measured concentration and the predetermined concentration is indicative of the porous material being non-integral.

BRIEF DESCRIPTION OF THE DRAWINGS

For a better understanding of the present disclosure, reference is made to the accompanying drawings, which are incorporated herein by reference and in which.

DETAILED DESCRIPTION

Before describing the embodiments in further detail, a number of terms will be defined.

As used herein, the singular forms "a", "an", and "the" include, plural referents unless the context clearly dictates otherwise.

The expression "integral" as used herein when referring to porous materials such as a porous single layer or porous membrane, porous multilayers, or a plurality of porous membranes, means a non-defective porous material.

The expression "non-integral" or as used herein when referring to porous materials such as a porous single layer or porous membrane, porous multilayers, and a plurality of porous membranes means a defective porous material. Non-limiting examples of defects in a porous layer or membrane include, but are not limited to, oversized pores, improper bonding (e.g., delamination or separation) between a plurality of porous layers or membranes that are bonded together to form a multilayer element, and defects on the porous layer or porous membrane.

The expression "porous material", as used herein, may include, but is not limited to, one or more porous membranes, sheets, rods, discs, tubes, layers, filters, filter elements, filtration media, containers, cylinders, cassettes, cartridges, columns, chips, beads, plates, monoliths, hollow fibers, and combinations thereof. The porous materials may be pleated, flat, spirally wound, and combinations thereof. It may be a single layered or multilayered membrane device. The membrane may be symmetric or asymmetric. The porous material may be contained in a housing, which may have an inlet and an outlet. It may be used for filtration of unwanted materials including contaminants such as infectious organisms and viruses, as well as environmental toxins and pollutants. The porous material may be comprised of any suitable material, including, but not limited to polyether sulfone, polyamide, e.g., nylon, cellulose, polytetrafluoroethylene, polysulfone, polyester, polyvinylidene fluoride, polypropylene, a fluorocarbon, e.g. poly (tetrafluoroethylene-co-perfluoro(alkyl vinyl ether)), poly carbonate, polyethylene, glass fiber, polycarbonate, ceramic, and metals.

Embodiments disclosed herein include a method for integrity testing porous materials, including porous single layer materials, porous materials having a multilayered configuration, porous membranes and filters. The porous material may be in a housing providing a feed or inlet side and a permeate or outlet side.

Figure 1:
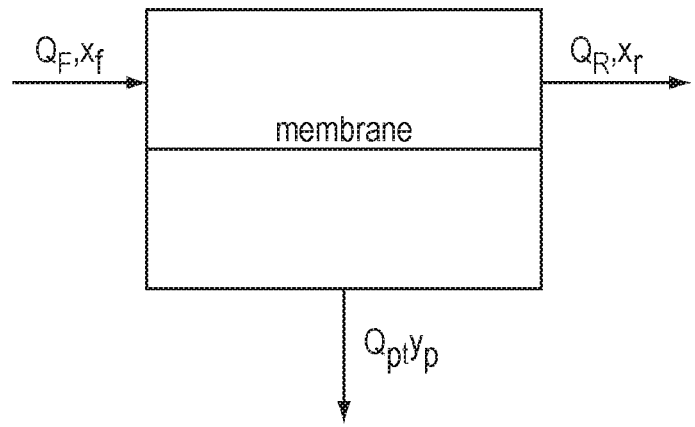
FIG. 1 is a schematic diagram of a flow configuration in a binary gas integrity test.

Turning now to FIG. 1, there is shown schematically a flow configuration in a binary gas integrity test. In a binary gas test, there is a feed (inlet) gas stream having at least two components in which one of the components permeates faster across the liquid filled membrane layer than a second component. The feed stream enters the upstream side of the membrane. The retentate stream, which is depleted of the faster permeating component, exits the upstream side of the membrane. The permeate stream, which is enriched in the faster permeating component, exits the downstream side of the membrane. In FIG. 1, $Q_F$ is the feed (inlet) flow rate, $Q_R$ is the retentate flow rate, $Q_p$ is the permeate flow rate, $X_f$ is the mole fraction of the faster permeating component in the feed stream, $X_r$ is the mole fraction of the faster permeating component in the retentate stream, and $y_p$ is the mole fraction of the faster permeating component in the permeate stream.

Conventionally, the integrity of the membrane filter is assessed by measuring concentration of the permeate stream. For an integral filter, the concentration of the faster permeating gas should be within an expected range (determined either theoretically or empirically). A leak from the inlet side to the permeate side will result in a change in the permeate concentration and this deviation of the concentration of the faster permeating gas from the expected value is a signal for a leak or non-integral membrane filter.

Since the binary gas test is a steady state process, however, in accordance with the embodiments disclosed herein, the concentration of the permeate gas can be determined from upstream measurements only. The composition of the permeate can be obtained by mass balance:

$$y_p = (Q_F x_f - Q_R x_r)/(Q_F - Q_R) \quad (1)$$

Thus, by measuring only the upstream inlet and upstream outlet flow rates and concentrations, the integrity of the membrane filter can be assessed. The presence of a leak (indicative of a non-integral filter) will reduce the concentration of the faster permeating component in the permeate gas because the permeate gas will be diluted with inlet gas (permeate gas that is enriched with the faster permeating component mixed with inlet side gas). For a system in which the gas is perfectly mixed on both sides of the membrane, the gas composition on the permeate side of an integral membrane is given by:

$$\frac{y_p}{1-y_p} = \frac{\alpha(x_r - Pr\, y_p)}{1 - x_r - Pr(1 - y_p)} \text{ and} \quad (2)$$

$$y_p = \frac{x_f - (1-\theta)x_r}{\theta} \quad (3)$$

where alpha is the ratio of the permeability of the fast gas to the permeability of the slow gas, Pr is the ratio of the permeate pressure to the feed pressure ($P_p/P_f$), and θ is the fraction of feed gas that has permeated the membrane ($Q_p/Q_f$ or $(Q_f-Q_r)/Q_f$). Using the foregoing three equations, the expected compositions of the permeate and retentate streams in an integral filter can be calculated. If there is a leak from the inlet side of the filter to the permeate side of the filter, the permeate concentration will be reduced according to:

$$y_{p,ni} = \frac{(Q_F - Q_R)y_p + Q_l x_f}{Q_F - Q_R + Q_l} \quad (4)$$

where $y_{p,ni}$ is the non-integral permeate concentration, and $Q_l$ is the leak rate.

In some embodiments, the predetermined concentration to which the measured concentrations are compared is the concentration expected from an integral porous material or device. The predetermined concentration may be the concentration of gas calculated to diffuse through an integral (i.e., non-defective), wetted porous material at a given temperature and pressure, or may be an actual concentration of gas that diffused through an integral wetted porous material at a given temperature and pressure.

In certain embodiments, the porous material is wetted with a liquid (a "wetting liquid") by saturating the porous material with the liquid. Suitable liquids include water, isopropyl alcohol and mixtures of isopropyl alcohol and water. Other liquids also could be used but may not be ideal due to cost and/or convenience.

Suitable temperatures for carrying out the integrity test range from about 4° C. to about 40° C., preferably between about 22-24° C. Suitable feed pressures range from about 15 psia to about 100 psia, preferably about 40-70 psia.

In certain embodiments, a plurality of gases, such as a low-cost binary gas pair, such as oxygen and nitrogen, available via compressed air, are used as the inlet gas to perform the test. Suitable amounts of each gas are not particularly limited. The gases should have different permeation rates through the liquid used to wet the porous material. The ratio of faster permeating gas to slower permeating gas in the gas mixture is influenced by a number of factors, including the ease of composition measurement, gas flow rate through the membrane, and economic considerations. In the case of air, the composition is fixed by ambient conditions. The composition of air on a dry basis is 20.95% $O_2$, 78.09% $N_2$, 0.93% Ar, 0.04% $CO_2$, and trace levels of other gases.

Example 1

Figure 2:
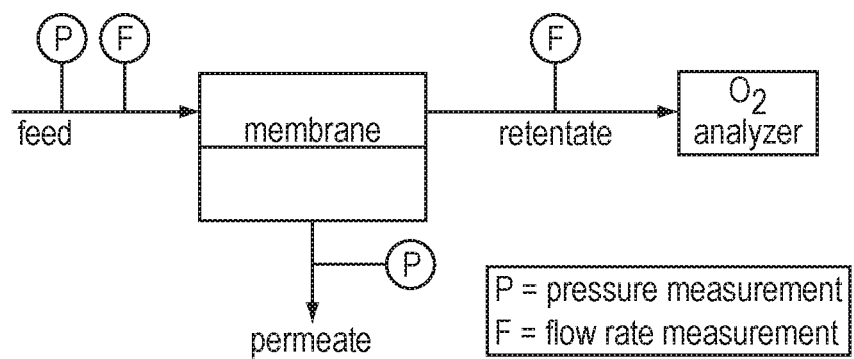
FIG. 2 is a schematic diagram of an integrity test arrangement in accordance with certain embodiments.

An experimental setup for an upstream side binary gas test is shown in FIG. 2. The tested filters were sterilizing grade PVDF filters in 10-inch pleated cartridge format from MilliporeSigma (CVGL Durapore® Cartridge Filter 10 in. 0.22 μm). Air (consisting primarily of oxygen and nitrogen) is a convenient feed gas to use owing to its low cost, easy accessibility, and safe use. In this testing, a synthetic air mixture of 21.38% $O_2$ and balance $N_2$ was used. Oxygen permeates through water at about twice the rate of $N_2$, so the permeate gas is expected to be oxygen enriched while the retentate gas is expected to be nitrogen enriched. The filter was wetted with water and the inlet gas was introduced to the filter at 40 psig. The permeate gas was vented to atmosphere. A metering valve was used to control the retentate flow rate, which was measured using a mass flow meter. The concentration of oxygen was measured with an oxygen analyzer (Servomex model 4100). For the retentate side testing, the retentate flow rate was held constant at about 88 sccm, which was suitable as a flow rate for the oxygen analyzer.

Three devices that had previously been determined by the prior art binary gas test to be clearly integral (passing), marginal non-integral (marginal failure) and clearly non-integral (failing) were tested per the above description and FIG. 2. The integrity results are summarized in Table 1 below:

TABLE 1

Integrity test results comparing prior art method to method of this invention.

| | | Prior art method (permeate side access) | | This invention (inlet side access only) | | |
|---|---|---|---|---|---|---|
| | | $y_p$ (%) | | | $x_r$ (%) | |
| Filter ID | Expected Integral | Measured | Integrity determination | Expected Integral | Measured | Integrity determination |
| 77 | 30.7 | 30.72 | Pass | 20.07 | 20.08 | Pass |
| 17 | 30.7 | 30.53 | Marginal fail | 20.08 | 20.20 | Marginal fail |
| 14 | 30.7 | 28.35 | Clear fail | 19.53 | 20.12 | Clear fail |

The method of the embodiments disclosed herein and the prior art method were in agreement for all three filters. In the prior art method, the expected integral concentration does not vary because θ is set to <<1%. As θ approaches zero, $y_p$ as a function θ approaches an asymptotic limit, and $x_r$ approaches $x_f$. This can be demonstrated from Equations 2-3. For the prior art method, operating in a region where $y_p$ is not sensitive to θ is preferred since at low θ any fluctuations in θ (resulting from fluctuations in $Q_f$, $Q_r$, or $Q_p$) will have minimal impact on the measurement of $y_p$. For the inlet side test, it is $Q_r$ that is fixed (88 sccm in this example) and θ is allowed to fluctuate. Therefore, as θ varies, $x_r$ varies in accordance with equations 2-3. The expected integral concentrations were calculated using a=2.1, Pr=0.27 and 8 based on the measured values of $Q_f$ and $Q_r$.

After completion of the integrity tests, each of the cartridges listed in Table 1 was tested for bacterial retention using the method described in ASTM F 838-05, incorporated herein by reference. The retention performance of a filter can be quantified with the log reduction value (LRV) defined as:

$$LRV = \text{Log}(C_i/C_f)$$

where $C_i$ and $C_f$ are the concentrations of bacteria in the inlet and filtrate streams, respectively. Filter 77 was completely retentive (no bacteria was found in the filtrate) and determined to have an LRV of >11.2. Filter 17 had an LRV of 7.8 and filter 14 had an LRV of 5.4 Thus, the bacterial retention tests were in alignment with the integrity test results.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method of integrity testing a porous material, comprising:
   providing a porous material to be tested, said porous material having an upstream side and a filtrate side;
   providing a gas stream comprising at least first and second gases having different permeabilities in a liquid used to wet said porous material;
   introducing said gas stream to said upstream side of said porous material;
   causing said first and second gases to flow through said porous material;
   measuring the concentration of at least one of said first and second gases in a retentate stream exiting said upstream side of said porous material; and
   comparing the measured concentration to a predetermined concentration;
   wherein a difference between said measured concentration and said predetermined concentration is indicative of said porous material being non-integral.

2. The method of claim 1, wherein said first gas is oxygen and said second gas is nitrogen.

3. The method of claim 1, wherein said first gas is oxygen, and wherein said concentration of one of said gases is measured with an oxygen analyzer.

4. The method of claim 1, wherein said liquid comprises water.

5. The method of claim 1, wherein said porous material is a sterilizing grade filter.

6. The method of claim 1, wherein said porous material comprises a membrane.

* * * * *